(12) United States Patent
Stokes

(10) Patent No.: US 6,727,438 B1
(45) Date of Patent: Apr. 27, 2004

(54) METHOD FOR DETERMINING OIL AND GREASE CONTENT USING A REFERENCE WEIGHT SIGNAL FOR LIVE CANCELLATION OF DISTURBANCES IN THE WEIGHTING SIGNAL

(76) Inventor: Steve Stokes, 116 Fountain Bend Dr., Lafayette, LA (US) 70506

( * ) Notice: Subject to any disclaimer, the term of this patent is extended or adjusted under 35 U.S.C. 154(b) by 146 days.

(21) Appl. No.: 10/146,839

(22) Filed: May 15, 2002

(51) Int. Cl.[7] .............................................. G01G 19/00
(52) U.S. Cl. ..................... 177/200; 177/185; 702/101; 436/8; 436/60
(58) Field of Search ............................... 177/185, 200; 702/101; 73/1.13; 436/8, 60

(56) References Cited

U.S. PATENT DOCUMENTS

| | | | |
|---|---|---|---|
| 4,212,361 A | 7/1980 | Stocker | 177/200 |
| 4,258,811 A | 3/1981 | Franzon et al. | 177/200 |
| 4,396,080 A | 8/1983 | Dee | 177/185 |
| 4,593,778 A | 6/1986 | Konishi et al. | 177/185 |
| 4,624,331 A | 11/1986 | Naito | 177/185 |
| 4,751,973 A | 6/1988 | Freeman et al. | 177/185 |
| 4,926,359 A | 5/1990 | Konishi et al. | 177/185 |
| 5,050,693 A | 9/1991 | Wirth et al. | 177/200 |
| 5,148,881 A | 9/1992 | Leisinger | 177/50 |
| 5,178,227 A | 1/1993 | Kvisgaard et al. | 177/200 |
| 5,294,553 A | 3/1994 | Kawahara | 436/60 |
| 5,487,702 A | 1/1996 | Campbell et al. | 460/7 |
| 5,550,328 A | 8/1996 | Freeman et al. | 177/50 |
| 5,936,206 A | 8/1999 | Tajiri | 177/25.13 |
| RE36,411 E | 11/1999 | Nakamura et al. | 177/185 |
| 6,013,879 A * | 1/2000 | Nakamura et al. | 177/25.13 |
| 6,283,853 B1 | 9/2001 | Pellenc et al. | 460/6 |

* cited by examiner

Primary Examiner—Randy W. Gibson
(74) Attorney, Agent, or Firm—Greg R. Mier; Joseph L. Lemoine; Jesse D. Lambert

(57) ABSTRACT

A method for determining the oil and grease concentration of aqueous solutions on offshore facilities without having to ship the aqueous solutions to shore-based laboratories for analysis. The method generally involves a liquid-liquid extraction procedure, where a concentration of oil and grease extracted from a known volume of aqueous solution is determined using a pair of weighing devices, which are connected to a common computer which is capable of processing synchronized data points received from the two weighing devices. The first weighing device is a control scale upon which a reference mass having a known weight is placed. The second weighing device is a sample scale upon which the extracted oil and grease will be placed. Any wave motion, vibration, and/or other environmental and/or physical condition on the offshore facility affecting the first weighing device will also affect the second weighing device in like fashion, and therefore will be compensated for when determining the true weight of the extracted oil and grease.

20 Claims, 3 Drawing Sheets

METHOD FOR DETERMINING OIL AND GREASE CONTENT USING A REFERENCE WEIGHT SIGNAL FOR LIVE CANCELLATION OF DISTURBANCES IN THE WEIGHTING SIGNAL

CROSS REFERENCE TO RELATED APPLICATIONS

Not applicable.

1. Field of the Invention

The subject invention relates to a method for determining the oil and grease content in an aqueous solution. More specifically, the subject invention relates to a method for measuring the oil and grease content in an aqueous solution on offshore oil and gas facilities, where persistent wave motion, vibration, and/or other environmental and/or physical conditions make conventional methods of measurement inadequate.

2. Description of Related Art

The U.S. Environmental Protection Agency ("EPA") and various state governments have enacted regulations and statutes to control the amount of oil and grease being discharged from oil and gas facilities engaged in operations such as production, field exploration, developmental drilling, well completion, and well treatment. For instance, the EPA authorizes operators engaged in such oil and gas operations off the coast of Louisiana to discharge "produced water" into the territorial seas of Louisiana, but only if the oil and grease concentration of the produced water has a daily maximum of 42 ppm and a monthly average of 29 ppm. See Final NPDES General Permit for Discharge from new and Existing Sources in the Offshore Subcategory of the Oil and Gas Extraction Category for the Territorial Seas of Louisiana (LAG260000). Other governmental agencies such as the Minerals Management Service may govern produced water discharge in Federal waters.

"Produced water" is partially derived from a natural water layer (called formation water) that typically lies underneath the hydrocarbons in reservoirs of oil and gas (although at times the water may be effectively intermingled with the hydrocarbons). To achieve maximum hydrocarbon recovery from these reservoirs, additional water is occasionally injected into the reservoirs to help force the hydrocarbons to the surface. Both the formation water and the injected water may be eventually produced along with the hydrocarbons. Hence, the name "produced water" applies to the formation water and injected water that is sometimes produced from oil and gas reservoirs.

At the surface, the produced water is separated from the hydrocarbons, and thereafter treated to remove as much oil and grease as possible. Even after treatment, however, the produced water still contains traces of oil and grease, which presents an environmental disposal problem that is closely monitored by the EPA and various federal and state entities, as discussed above. Thus, for the purpose of regulatory compliance and process control, measurement of oil and grease in produced water has been and will remain a very important aspect of the oil and gas industry.

The EPA recommends that laboratories use a liquid-liquid extraction procedure for determining the oil and grease content in produced water. During a typical liquid-liquid extraction procedure, a solvent is added to a known volume of produced water containing some amount of oil and grease. The solvent extracts the oil and grease, and the solvent is thereafter separated from the produced water. Next, the solvent is evaporated until all that remains is the extracted oil and grease. The weight of the extracted oil and grease is then compared to the volume of the produced water to determine the oil and grease concentration.

For oil and gas operations, especially those operations performed offshore, where constant wave motion, vibration, and/or other environmental and/or physical conditions are prevalent, obtaining an accurate weight of the extracted oil and grease during the final stages of the liquid-liquid extraction procedure has proven to be very difficult. Conventional weighing devices typically used for this application are incapable of providing accurate measurements unless they are level and stationary, two conditions which infrequently occur on offshore facilities.

To avoid the effects of constant wave motion, vibration, and/or other environmental and/or physical conditions, offshore operators currently ship their produced water samples to shore-based laboratories for oil and grease analysis. The shipment of these samples to shore-based laboratories, either by boat or helicopter, is time consuming and costly. Shipping by boat is relatively slow and limited by rough sea conditions. Shipping by helicopter is very expensive and limited by inclement weather and nighttime conditions. Delays associated with the shipment of samples can result in forced production downtime with the attendant loss of revenue. It is readily seen, therefore, that accurate, reliable oil and grease measurement has tremendous economic incentives.

The present invention provides a method for determining the oil and grease content of an aqueous stream generated from an offshore facility, with the measurement being conducted on the offshore facility without having to ship samples of the produced water to shore-based laboratories for analysis. The present invention discloses a method by which samples can be analyzed offshore, regardless of the wave motion, vibration, and/or other environmental and/or physical conditions that are prevalent offshore. The present invention therefore avoids the potential time delays and costs associated with the shipment of samples from offshore operations to shore-based laboratories.

The related prior art references include U.S. Pat. No. 5,294,553, issued to Kawahara on Mar. 15, 1994, which discloses a method of gravimetric determination of grease and oil in an aqueous matrix, comprising the steps of preparing a sample, extracting the grease and oil using a non-halogenated solvent mixture, distilling and evaporating the solvent, and weighing the extraction residue.

Another related prior art reference is U.S. Pat. No. 5,178,227, issued to Kvisgaard on Jan. 12, 1993, which discloses a maritime weighing system that makes corrections for errors due to tiltings of the ship and due to the mechanical noise produced by the engine of the ship or by operative implements on the ship.

None of these prior art references, nor any of the prior art references listed in the Applicant's Information Disclosure Statement, disclose the method of the present invention.

SUMMARY OF THE INVENTION

The present invention provides a method for determining the oil and grease concentration of aqueous solutions on an offshore facility without having to ship the aqueous solutions to shore-based laboratories for analysis. The method of the present invention generally involves a liquid-liquid extraction procedure, where the weight of oil and grease extracted from a known volume of aqueous solution is determined using a pair of weighing devices, which are connected to a common computer that is capable of processing synchronized data points received from the two weighing devices.

The first weighing device is a control scale upon which a known weight is placed. The second weighing device is a sample scale upon which the extracted oil and grease is placed. Any wave motion, vibration, and/or other environmental and/or physical condition on the offshore facility affecting the first weighing device will also affect the second weighing device in like fashion, and therefore will be compensated for when determining the true weight of the oil and grease. The present method allows the aqueous solution samples to be analyzed offshore and, therefore, eliminates the time delays and costs associated with the shipment of samples from offshore facilities to shore-based laboratories.

BRIEF DESCRIPTION OF THE DRAWINGS

The invention will be better understood by reference to the accompanying drawings wherein.

DESCRIPTION OF THE INVENTION

While the present invention will be described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore, it is intended that the present invention not be limited to the particular embodiments disclosed as the best mode contemplated for carrying out this invention, but that the invention will include all embodiments (and legal equivalents thereof) falling within the scope of the appended claims.

The method of the present invention generally involves a liquid-liquid extraction procedure, where a concentration of oil and grease extracted from a known volume of aqueous solution is determined using a pair of weighing devices 20 and 30, which are connected to a common computer 10 that is capable of processing synchronized data points received from weighing devices 20 and 30.

Liquid-Liquid Extraction Procedure

The first general step of the liquid-liquid extraction procedure ("the procedure") is to obtain a known volume (approximately one liter) of an aqueous solution to be analyzed for oil and grease content. The aqueous solution sample is preferably obtained in a glass container and should be maintained at approximately 72° F. during the procedure. The pH of the aqueous solution sample should be no greater than 2. An appropriate amount of hydrochloric acid should be added to the sample, if necessary, to obtain a pH of no greater than 2.

The next general step of the procedure is to thoroughly mix a known volume (preferably 30 milliliters) of a suitable solvent (n-hexane, for example) into the aqueous solution sample. The mixing process allows the solvent to extract the oil and grease from the aqueous solution. After thorough mixing, the mixture should be allowed to settle until substantially all of the solvent, along with the extracted oil and grease contained therein, forms a liquid layer on top of the aqueous solution. The solvent, along with the extracted oil and grease, is then separated from the aqueous solution into a pre-weighed container or flask.

The next general step of the procedure is to evaporate the solvent, leaving in the container or flask only the oil and grease extracted from the aqueous solution. Once the container containing the extracted oil and grease is cooled to approximately 72° F., the container is weighed a second time to determine the amount of extracted oil and grease remaining in the container. The weight of the extracted oil and grease can then be compared to the volume of the aqueous solution sample to compute the concentration of oil and grease in the aqueous solution.

Weighing Devices 20 and 30

Figure 1:
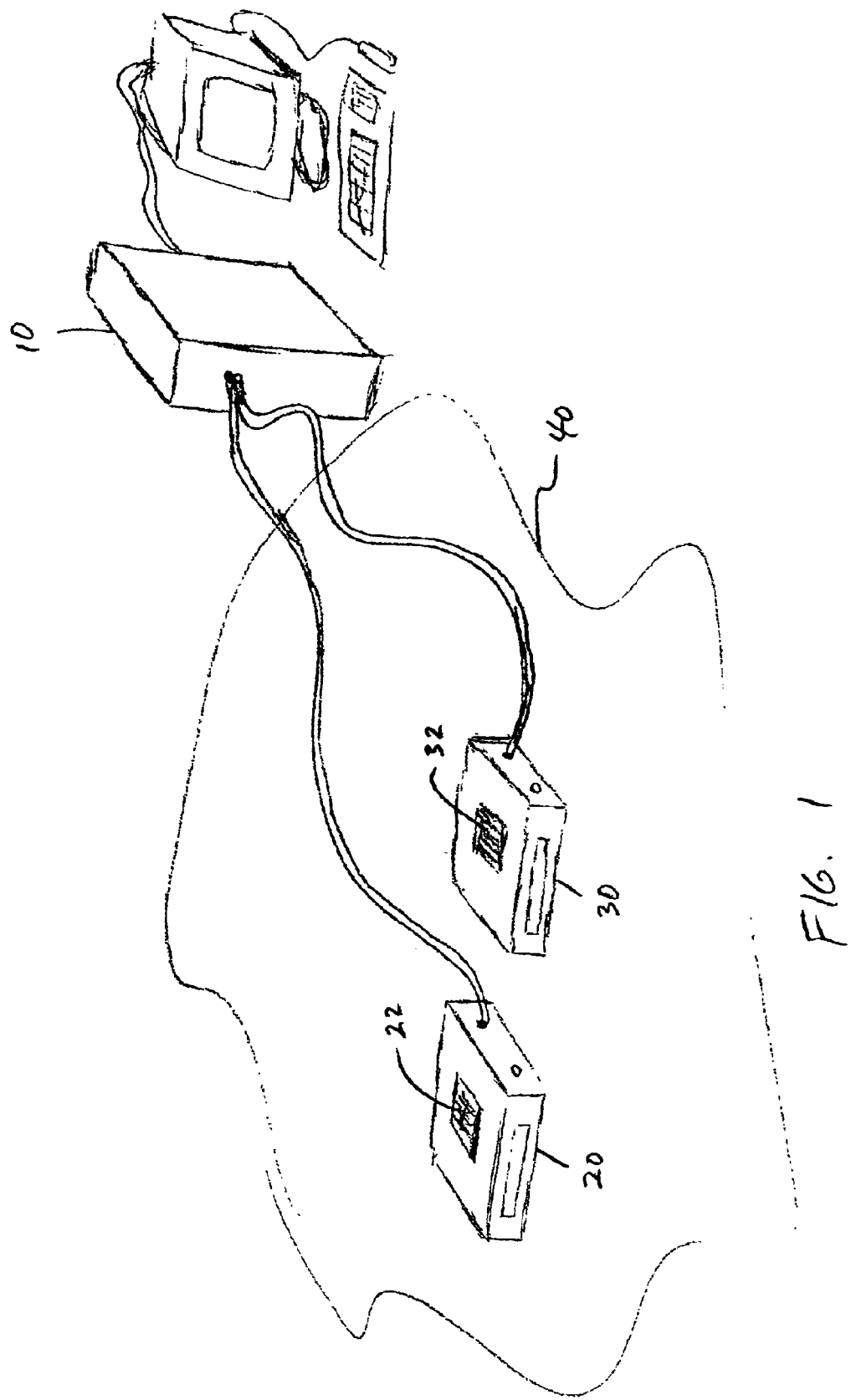
FIG. 1 is a schematic diagram of the major components used in the method of the present invention.

The weighing steps during the liquid-liquid extraction procedure generally described above are preferably performed using first and second weighing devices 20 and 30, as shown in FIG. 1. First and second weighing devices 20 and 30 are preferably digital data transfer scales fixably mounted in close proximity to each other. First and second weighing devices 20 and 30 are preferably identical, and should be capable of producing synchronized sample data outputs at a preferred rate of approximately 0.1 to 0.15 seconds per data point, or approximately 6 to 10 synchronized data points per second. First and second weighing devices 20 and 30 are preferably accurate to +or −0.1 milligrams.

First and second weighing devices 20 and 30 are preferably equipped with weighing pans or platforms 22 and 32, respectively, which should be as light as possible so that their weight does not noticeably affect the data output from weighing devices 20 and 30 as a result of any wave motion, vibration, and/or other environmental and/or physical condition on the offshore facility. When nothing is placed on weighing pans 22 and 32, the data output from weighing devices 20 and 30, respectively, should be zero. If the value of the data output is not zero under these conditions, manually operable adjustment knobs 23 and 33 should be available on weighing devices 20 and 30, respectfully, to adjust the data output accordingly.

Figure 2:
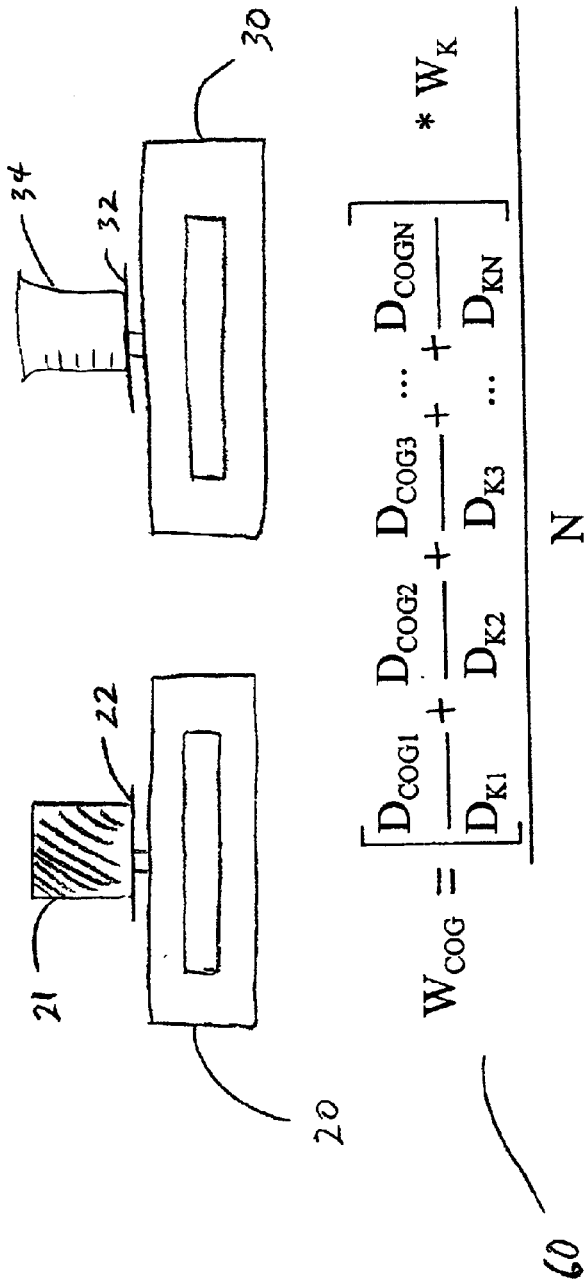
FIG. 2 is a representation of the formula used to compensate for wave motion, vibration, and/or any other environmental and/or physical conditions prevalent on offshore facilities.

Referring to FIG. 2, first weighing device 20 is a control scale upon which a reference mass 21 having a known weight ($W_K$) will be placed during the weighing steps of the liquid-liquid extraction procedure generally described above. The known weight ($W_K$) of reference mass 21 should approximately equal the weight ($W_C$) of the container 34 used to receive the solvent, as discussed above, plus the mean weight ($W_{OG}$) of the oil and grease typically extracted from the approximately one liter sample of aqueous solution.

Still referring to FIG. 2, second weighing device 30 is a sample scale upon which container 34 will be placed on two separate occasions during the liquid-liquid extraction procedure—once before the solvent is added and again after the solvent is evaporated. Before the solvent is added, second weighing device 30 should be used to determine the weight ($W_C$) of empty container 34. Afterwards, when the solvent has been added to container 34 and later evaporated therefrom, leaving only the oil and grease extracted from the aqueous solution, second weighing device 30 should be used to determine the weight ($W_{COG}$) of container 34 plus the extracted oil and grease. The weight $W_C$ of empty container or flask 34 can then be subtracted from the weight ($W_{COG}$) of container 34 plus the extracted oil and grease to determine the net weight ($W_{OG}$) of the oil and grease extracted from the aqueous solution.

Computer 10

As shown in FIG. 1, first and second weighing devices 20 and 30 are preferably connected to an electronic computer 10, having data acquisition software. The data acquisition software should be able to process data received from weighing devices 20 and 30, respectively, and perform the calculation depicted in the formula 60 shown in FIG. 2. According to formula 60, for each set of synchronized data points received from first and second weighing devices 20 and 30, computer 10 should divide the output signal ($D_{COG1}$, $D_{COG2}$, etc.) from weighing device 30 by the output signal ($D_{K1}$, $D_{K2}$, etc.) from weighing device 20 to obtain a synchronized data point quotient. Once this calculation has been performed for a pre-determined number (N) of synchronized data points, all of the synchronized data point quotients should be added together to obtain a sum of said synchronized data point quotients, which sum should be divided by the pre-determined number (N) of synchronized data points, and then multiplied by the weight ($W_K$) of the known reference mass 21 to obtain an adjusted sample weight ($W_C$ or $W_{COG}$).

By using formula 60 in FIG. 2, any wave motion, vibration, and/or other environmental and/or physical condition on the offshore facility affecting the data received from second weighing device 30 will also affect the data received from first weighing device 20 in like fashion, and therefore will be compensated for by the time integration of the two synchronized data output signals received from first and second weighing devices 20 and 30.

Surface 40

Figure 3:
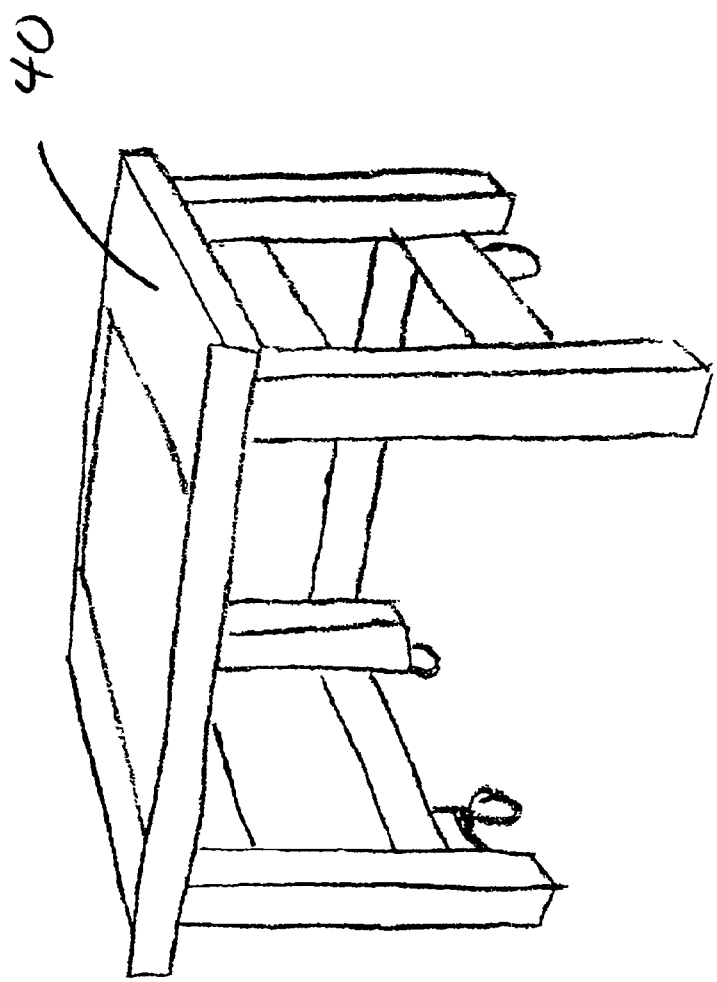
FIG. 3 is a schematic of a vibration-free table.

Surface 40 upon which first and second weighing devices 20 and 30 may be placed can be any accessible surface which is suitable for supporting first and second weighing devices 20 and 30. Surface 40 is preferably a horizontal table or counter top which is vibration and movement free, although it is acknowledged that such surfaces are typically not available on offshore facilities. Vibration-free table tops, such as the 63–500 series high-performance lab tables manufactured and marketed by Technical Manufacturing Corporation as shown in FIG. 3, are commercially available and can be utilized as surface 40 for the method of the present invention.

Advantages of the Present Invention

Based on the foregoing, the reader will see that the present invention provides a novel method by which the oil and grease content of an aqueous solution can be determined on an offshore facility, despite the constant wave motion, vibration, and/or other environmental and/or physical conditions that can adversely affect the results of the oil and grease analysis. The present method allows the aqueous solution samples to be analyzed offshore and, therefore, eliminates the time delays and costs associated with the shipment of samples from offshore facilities to shore-based laboratories.

While the above description contains many specificities, these should not be construed as limitations on the scope of the invention, but rather as an exemplification of one preferred embodiment thereof. Accordingly, the scope of the present invention should be determined not by the embodiment(s) illustrated, but by the appended claims and their legal equivalents.

What is claimed is:

1. A method for determining a concentration of oil and grease in an aqueous solution, comprising the steps of:
    (a) extracting said oil and grease from a known volume of aqueous solution;
    (b) connecting a first weighing device and a second weighing device to a computer, each of said weighing devices having readable outputs in response to weights placed thereon;
    (c) placing the oil and grease on the first weighing device and a known weight on the second weighing device;
    (d) using the computer to compare the readable outputs from the first and second weighing devices to determine an actual weight of the oil and grease; and
    (e) dividing said weight of the oil and grease by the known volume of the aqueous solution.

2. The method of claim 1, wherein the first and second weighing devices are in close proximity to each other.

3. The method of claim 2, wherein the first and second weighing devices are digital data transfer scales.

4. The method of claim 3, wherein the first and second weighing devices are capable of producing synchronized data outputs at 6 to 10 data points per second.

5. The method of claim 4, wherein the pH of aqueous solution is adjusted to no greater than 2.

6. The method of claim 5, wherein the first and second weighing devices are identical.

7. The method of claim 1, where said method is performed in an offshore environment.

8. A method for determining a concentration of oil and grease in an aqueous solution, the method to be conducted on an offshore facility, comprising the steps of:
    (a) obtaining a known volume of aqueous solution having an unknown amount of oil and grease;
    (b) mixing a suitable solvent into the aqueous solution so that the solvent extracts the oil and grease from the aqueous solution;
    (c) separating the solvent and extracted oil and grease from the aqueous solution;
    (d) evaporating the solvent containing the extracted oil and grease, leaving only said oil and grease;
    (e) connecting a first weighing device and a second weighing device to a computer, each of said weighing devices having readable outputs in response to weights placed thereon;
    (f) placing the oil and grease on the first weighing device and a known weight on the second weighing device;
    (g) using the computer to compare the readable outputs from the first and second weighing devices to determine a weight of the oil and grease; and
    (h) dividing said weight of the oil and grease by the volume of the aqueous solution, thereby determining a mass/volume concentration.

9. The method of claim 8, wherein the solvent is n-hexane.

10. The method of claim 8, wherein the first and second weighing devices are in close proximity to each other.

11. The method of claim 10, wherein the first and second weighing devices are digital data transfer scales.

12. The method of claim 11, wherein the first and second weighing devices are capable of producing synchronized data outputs at 6 to 10 data points per second.

13. The method of claim 12, wherein the pH of aqueous solution is adjusted to no greater than 2.

14. The method of claim 13, wherein the first and second weighing devices are identical.

15. A method for determining a concentration of oil and grease in an aqueous solution, the method to be conducted on an offshore facility, comprising the steps of:

(a) obtaining a known volume of aqueous solution having an unknown amount of oil and grease;

(b) mixing a suitable solvent into the aqueous solution so that the solvent extracts the oil and grease from the aqueous solution;

(c) allowing the solvent and oil and grease to form a liquid layer on top of the aqueous solution;

(d) separating the solvent and oil and grease from the aqueous solution, and placing the solvent and oil and grease into a container having a known weight;

(e) evaporating the solvent from the container, leaving therein only the oil and grease;

(f) placing a first weighing device and a second weighing device, each having computer readable outputs therefrom in response to weights placed thereon, on a surface in close proximity to one another, and connecting said first and second weighing devices to a computer;

(g) placing said container holding the oil and grease on the first weighing device and a known weight on the second weighing device;

(h) using the computer to compare the readable outputs from the first and second weighing devices to determine a combined weight of said container and oil and grease;

(i) calculating a weight of the oil and grease by subtracting the weight of the container from the combined weight of the container and oil and grease; and (j) dividing said weight of the oil and grease by the volume of the aqueous solution, thereby determining a mass/volume concentration of said oil and grease.

16. The method of claim 15, wherein the surface is a vibration-free table.

17. The method of claim 16, wherein the solvent is n-hexane.

18. The method of claim 17, wherein the first and second weighing devices are digital data transfer scales.

19. The method of claim 18, wherein the first and second weighing devices are capable of producing synchronized data outputs at 6 to 10 data points per second.

20. The method of claim 19, wherein the first and second weighing devices are identical.

* * * * *